United States Patent [19]

Huang et al.

[11] Patent Number: 5,348,559
[45] Date of Patent: Sep. 20, 1994

[54] COPPER-CONTAINING AROMATIC MANNICH COMPLEXES AND CONCENTRATES AND DIESEL FUELS CONTAINING SAME

[75] Inventors: Nai Z. Huang, Mayfield Hts.; Christopher I. Kolp, Euclid; Christopher R. Sgarlata, Cleveland, all of Ohio

[73] Assignee: The Lubrizol Corporation, Cleveland, Ohio

[21] Appl. No.: 143,320

[22] Filed: Oct. 26, 1993

Related U.S. Application Data

[62] Division of Ser. No. 973,135, Nov. 6, 1992, Pat. No. 5,279,627.

[51] Int. Cl.$^5$ .............................................. C10L 1/30
[52] U.S. Cl. ........................................ 44/367; 44/358; 44/363
[58] Field of Search .................................. 44/367, 358

[56] References Cited

U.S. PATENT DOCUMENTS

| | | | |
|---|---|---|---|
| 3,346,493 | 10/1967 | Le Suer | 252/32.5 |
| 3,355,270 | 11/1967 | Amick | 44/367 |
| 3,945,933 | 3/1976 | Chibnik et al. | 252/33.3 |
| 3,980,569 | 9/1976 | Pinder et al. | 252/51.5 R |
| 4,093,614 | 6/1978 | Chibnik et al. | 260/299 |

(List continued on next page.)

FOREIGN PATENT DOCUMENTS

| | | |
|---|---|---|
| 0182940 | 6/1986 | European Pat. Off. |
| 0261795 | 3/1988 | European Pat. Off. |
| 1546216 | 11/1968 | France |
| 8701721 | 3/1987 | PCT Int'l Appl. |

(List continued on next page.)

OTHER PUBLICATIONS

Search Report for European Appl. 93117914.7, mailed Jan. 5, 1994.
Wiedemann et al, "Application of Particulate Traps & Fuel Additives for Reduction of Exhaust Emissions", SAE Tech. Paper, 840078, Feb. 27 to Mar. 2, 1984.
Simon et al, "Diesel Particular Trap Regeneration Using Ceramic Wall-Flow Traps, Fuel Additives, & Supplemental Electrical Igniters", SAE Tech. Paper 850016, Feb. 25-Mar. 1, 1985.
Covitch et al, "Oil Thickening in the Mack T-7 Engine Test-Fuel Effects . . . ", SAE Tech. Paper 852126, Oct. 21-24, 1985.
Covitch, "Oil Thickening in the Mack T-7 Engine Test. II-Effects of Fuel Composition on Soot Chemistry", (List continued on next page.)

*Primary Examiner*—Ellen M. McAvoy
*Attorney, Agent, or Firm*—Frederick D. Hunter

[57] ABSTRACT

This invention relates to copper-containing aromatic Mannich complexes, and to concentrates and diesel fuels containing said complexes. The diesel fuels are useful with diesel engines equipped with exhaust system particulate traps. The copper-containing aromatic Mannich complex is used for lowering the ignition temperature of exhaust particles collected in the trap. The copper-containing aromatic Mannich complex is made by contacting either component (A) or component (B) with component (C);

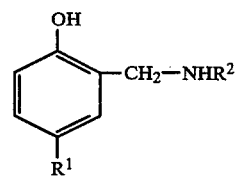

wherein $R^1$ is an alkyl group of 1 to about 6 carbon atoms, and $R^2$ is a saturated or unsaturated aliphatic hydrocarbyl group of about 16 to about 20 carbon atoms;

component (B) being a mixture of (B)(I) and (B)(II), component (B)(I) being at least one compound represented by the formula

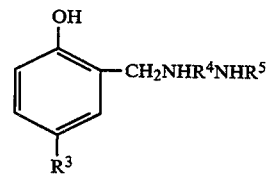

wherein $R^3$ is an alkyl group of about 9 to about 18 carbon atoms, $R^4$ is an alkylene group of 1 to about 4 carbon atoms, and $R^5$ is a saturated or unsaturated aliphatic hydrocarbyl group of about 16 to about 20 carbon atoms; and component (B)(II) being at least one compound represented by the formula

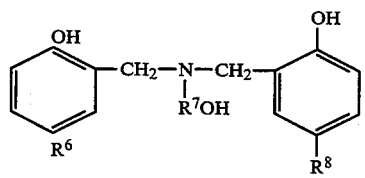

wherein $R^6$ and $R^8$ are independently alkyl groups of about 9 to about 18 carbon atoms, and $R^7$ is an alkylene group of 1 to about 4 carbon atoms; and
component (C) is at least one copper reactant.

13 Claims, No Drawings

U.S. PATENT DOCUMENTS

| | | | |
|---|---|---|---|
| 4,225,448 | 9/1980 | Braid | 252/42.7 |
| 4,505,718 | 3/1985 | Dorer | 44/66 |
| 4,552,677 | 11/1985 | Hopkins | 252/33.6 |
| 4,655,037 | 4/1987 | Rao | 60/274 |
| 4,664,677 | 5/1987 | Dorer et al. | 44/68 |
| 4,673,412 | 6/1987 | Stoldt et al. | 44/68 |
| 4,816,038 | 3/1989 | Koch et al. | 44/367 |
| 4,828,733 | 5/1989 | Faraq et al. | 252/42.7 |
| 4,867,890 | 9/1989 | Colclough et al. | 252/327 E |
| 5,279,627 | 1/1994 | Huang et al. | 44/367 |

FOREIGN PATENT DOCUMENTS

| | | |
|---|---|---|
| WO8802392 | 4/1988 | PCT Int'l Appl. . |
| 9220763 | 11/1992 | PCT Int'l Appl. . |
| 794015 | 1/1981 | U.S.S.R. . |
| 2064547 | 6/1981 | United Kingdom . |
| 2116583 | 9/1983 | United Kingdom . |
| 2248068 | 3/1992 | United Kingdom . |

OTHER PUBLICATIONS

SAE Tech. Paper 880259, Feb. 29–Mar. 4, 1988.

Levin et al. "An Experimental Evaluation to Determine the Effect of an Organometallic Fuel Additive . . . ", SAE Tech. Paper 900920, Apr. 3–5, 1990.

Stiglic et al, "Emission Testing of Two Heavy Duty Diesel Engines Equipped with Exhaust Aftertreatment", SAE Tech. Paper 900919, Apr. 3–5, 1990.

Pistillo et al, "Lubrication of Low Emission Diesel Engines", SAE Tech. Paper 902178, Oct. 22–25, 1990.

Winsor, "New Diesels Means New Demands on Oil, Fuel", Technology War on Emissions, Reprinted from Heavy Duty Trucking, May 1990.

"An Analysis of Possible Health, Effects Due to the Use of a Copper Diesel Fuel Additive", Roth Associates Inc, May 1990.

Environmental Protection Agency, Federal Reg., vol. 55, No. 162, Aug. 21, 1990, "Regulation of Fuels and Fuel Additives: Fuel Quality Regulations for Highway Diesel Fuel Sold in 1993 and Later Calendar Years", pp. 34120–34151.

COPPER-CONTAINING AROMATIC MANNICH COMPLEXES AND CONCENTRATES AND DIESEL FUELS CONTAINING SAME

This is a continuation, division, of application Ser. No. 07/973,135, filed Nov. 6, 1992, now U.S. Pat. No. 5,279,627.

TECHNICAL FIELD OF THE INVENTION

This invention relates to copper-containing aromatic Mannich complexes, and to concentrates and diesel fuels containing said complexes. The diesel fuels are useful with diesel engines equipped with exhaust system particulate traps. The copper-containing aromatic Mannich complexes are used to lower the ignition temperature of exhaust particles collected in the trap.

BACKGROUND OF THE INVENTION

Diesel engines have been employed as engines for over-the-road vehicles because of relatively low fuel costs and improved mileage. However, because of their operating characteristics, diesel engines discharge a larger amount of carbon black particles or very fine condensate particles or agglomerates thereof as compared to the gasoline engine. These particles or condensates are sometimes referred to as "diesel soot", and the emission of such particles or soot results in pollution and is undesirable. Moreover, diesel soot has been observed to be rich in condensed, polynuclear hydrocarbons, and some of these have been recognized as carcinogenic. Accordingly, particulate traps or filters have been designed for use with diesel engines that are capable of collecting carbon black and condensate particles.

Conventionally, the particulate traps or filters have been composed of a heat-resistant filter element which is formed of porous ceramic or metal fiber and an electric heater for heating and igniting carbon particulates collected by the filter element. The heater is required because the temperatures of the diesel exhaust gas under normal operating conditions are insufficient to burn off the accumulated soot collected in the filter or trap. Generally, temperatures of about 450°–600° C. are required, and the heater provides the necessary increase of the exhaust temperature in order to ignite the particles collected in the trap and to regenerate the trap. Otherwise, there is an accumulation of carbon black, and the trap is eventually plugged causing operational problems due to exhaust back pressure buildup. The above-described heated traps do not provide a complete solution to the problem because the temperature of the exhaust gases is lower than the ignition temperature of carbon particulates while the vehicle runs under normal conditions, and the heat generated by the electric heater is withdrawn by the flowing exhaust gases when the volume of flowing exhaust gases is large. Alternatively, higher temperatures in the trap can be achieved by periodically enriching the air/fuel mixture burned in the diesel engine thereby producing a higher exhaust gas temperature. However, higher temperatures can cause run-away regeneration leading to high localized temperatures which can damage the trap.

It also has been suggested that the particle build-up in the traps can be controlled by lowering the ignition temperature of the particulates so that the particles begin burning at the lowest possible temperatures. One method of lowering the ignition temperature involves the addition of a combustion improver to the exhaust particulate, and the most practical way to effect the addition of the combustion improver to the exhaust particulate is by adding the combustion improver to the fuel. Copper compounds have been suggested as combustion improvers for fuels including diesel fuels.

The U.S. Environmental Protection Agency (EPA) estimates that the average sulfur content of on-highway diesel fuel is approximately 0.25% by weight and has required this level be reduced to no more than 0.05% by weight by Oct. 1, 1993. The EPA has also required that this diesel fuel have a minimum cetane index specification of 40 (or meet a maximum aromatics level of 35%). The objective of this rule is to reduce sulfate particulate and carbonaceous and organic particulate emissions. See, Federal Register, Vol. 55, No. 162, Aug. 21, 1990, pp. 34120–34151. Low-sulfur diesel fuels and technology for meeting these emission requirements have not yet been commercially implemented. One approach to meeting these requirements is to provide a low-sulfur diesel fuel additive that can be effectively used in a low-sulfur diesel fuel environment to reduce the ignition temperatures of soot that is collected in the particulate traps of diesel engines.

U.S. Pat. No. 3,346,493 discloses lubricating compositions containing metal complexes made of the reaction products of hydrocarbon-substituted succinic acid (e.g., polyisobutylene-substituted succinic anhydride) compounds and alkylene amines (e.g., polyalkylene polyamines), the complexes being formed by reacting at least about 0.1 equivalent of a complex-forming metal compound with the reaction products. The metals are those having atomic numbers from 24 to 30 (i.e., Cr, Mn, Fe, Co, Ni, Cu and Zn).

U.S. Pat. No. 4,673,412 discloses fuel compositions (e.g., diesel fuels, distillate fuels, heating oils, residual fuels, bunker fuels) containing a metal compound and an oxime. The reference indicates that fuels containing this combination are stable upon storage and effective in reducing soot formation in the exhaust gas of an internal combustion engine. A preferred metal compound is a transition metal complex of a Mannich base, the Mannich base being derived from (A) an aromatic phenol, (B) an aldehyde or a ketone, and (C) a hydroxyl- and/or thiol-containing amine. Desirable metals are identified as being Cu, Fe, Zn, Co, Ni and Mn.

U.S. Pat. No. 4,816,038 discloses fuel compositions (e.g., diesel fuels, distillate fuels, heating oils, residual fuels, bunker fuels) containing the reaction product of a transition metal complex of a hydroxyl- and/or thiol-containing aromatic Mannich with a Schiff base. The reference indicates that fuels containing this combination are stable upon storage and effective in reducing soot formation in the exhaust gas of an internal combustion engine. The Mannich is derived from (A) a hydroxyl- and/or thiol-containing aromatic, (B) an aldehyde or a ketone, and (C) a hydroxyl- and/or thiol-containing amine. Desirable metals are identified as being Cu, Fe, Zn and Mn.

International Publication No. WO 88/02392 discloses a method for operating a diesel engine equipped with an exhaust system particulate trap to reduce the build-up of exhaust particles collected in the trap. The method comprises operating the diesel engine with a fuel containing an effective amount of a titanium or zirconlure compound or complex to lower the ignition temperature of the exhaust particulates collected in the trap.

SUMMARY OF THE INVENTION

This invention relates to copper-containing aromatic Mannich complexes, and to concentrates and diesel fuels containing said complexes. The diesel fuels are useful with diesel engines equipped with exhaust system particulate traps. The copper-containing aromatic Mannich complex is used for lowering the ignition temperature of exhaust particles collected in the trap. The copper-containing aromatic Mannich complex is made by contacting either component (A) or component (B) with component (C);

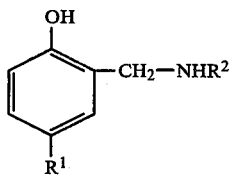

wherein $R^1$ is an alkyl group of 1 to about 6 carbon atoms, and $R^2$ is a saturated or unsaturated aliphatic hydrocarbyl group of about 16 to about 20 carbon atoms;

component (B) being a mixture of (B)(I) and (B)(II), component (B)(I) being at least one compound represented by the formula

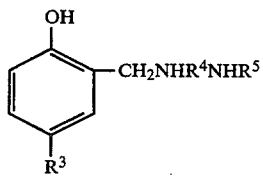

wherein $R^3$ is an alkyl group of about 9 to about 18 carbon atoms, $R^4$ is an alkylene group of 1 to about 4 carbon atoms, and $R^8$ is a saturated or unsaturated aliphatic hydrocarbyl group of about 16 to about 20 carbon atoms; and component (B)(II) being at least one compound represented by the formula

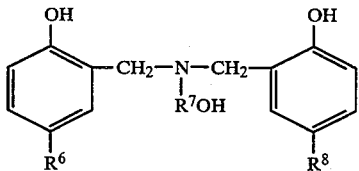

wherein $R^6$ and $R^8$ are independently alkyl groups of about 9 to about 18 carbon atoms, and $R^7$ is an alkylene group of 1 to about 4 carbon atoms; and component (C) is at least one copper reactant.

DESCRIPTION OF THE PREFERRED EMBODIMENTS

The aromatic Mannich complexes of the invention are soluble or stably dispersible in diesel fuel. The complexes that are soluble in diesel fuel are soluble to the extent of at least one gram per liter at 25° C. The complexes that are stably dispersible or stably dispersed in diesel fuel remain dispersed in said diesel fuel for at least about 24 hours at 25° C.

Component (A) is at least one compound represented by the formula

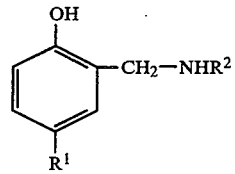

wherein $R^1$ is an alkyl group of 1 to about 6 carbon atoms, preferably about 3 to about 5 carbon atoms, more preferably about 4 carbon atoms; and $R^2$ is a saturated or unsaturated aliphatic hydrocarbyl group of about 16 to about 20 carbon atoms, preferably about 18 carbon atoms. In one embodiment $R^1$ is t-butyl. $R^2$ can be oleyl, palmityl, stearyl, arachidyl, palmitoleyl, linoleyl or linolenyl, with oleyl being preferred. $R^2$ can be a mixture of two or more of the foregoing hydrocarbyl groups, an example of which is tallow.

Component (B)(I) is at least one compound represented by the formula

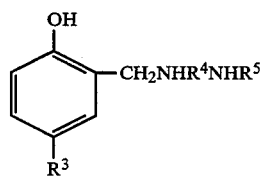

wherein $R^3$ is an alkyl group of about 9 to about 18 carbon atoms, preferably about 10 to about 14 carbon atoms, more preferably about 12 carbon atoms; $R^4$ is an alkylene group of 1 to about 4 carbon atoms, preferably 2 or 3 carbon atoms; and $R^5$ is a saturated or unsaturated aliphatic hydrocarbyl group of about 16 to about 20 carbon atoms, preferably about 18 carbon atoms. In one embodiment $R^1$ is dodecyl or propylene tetramer. In one embodiment $R^4$ is propylene or trimethylene. $R^5$ can be oleyl, palmityl, stearyl, arachidyl, palmitoleyl, linoleyl or linolenyl, with oleyl being preferred. $R^5$ can be a mixture of two or more of the foregoing hydrocarbyl groups, an example of which is tallow.

Component (B)(II) is at least one compound represented by the formula

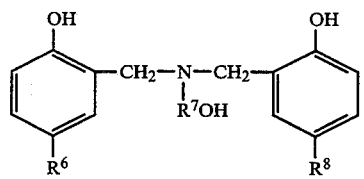

wherein $R^6$ and $R^8$ are independently alkyl groups of about 9 to about 18 carbon atoms, preferably about 10 to about 14 carbon atoms, more preferably about 12 carbon atoms; and $R^7$ is an alkylene group of 1 to about 4 carbon atoms, preferably 2 or 3 carbon atoms. In one embodiment $R^6$ and $R^8$ are dodecyl or propylene tetramer. In one embodiment $R^7$ is ethylene.

The aromatic Mannichs (A), (B)(I) and (B)(II) are derived from an alkyl-substituted phenol, formaldehyde or a precursor thereof (e.g., paraformaldehyde), and an amine.

The phenol is a compound having the formula

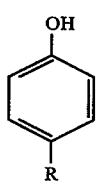

wherein R is $R^1$, $R^3$, $R^6$ or $R^8$ as defined above. The formaldehyde is preferably paraformaldehyde.

When the aromatic Mannich is component (A) the amine is a compound represented by the formula $$H_2NR^2$$

wherein $R^2$ is as defined above. In one embodiment this amine is oleylamine. The molar ratio of phenol to formaldehyde to amine is preferably about 1:1:1.

When the aromatic Mannich is component (B)(I) the amine is a compound represented by the formula $$H_2NR^4NHR^5$$

wherein $R^4$ and $R^5$ are as defined above. In one embodiment this amine is N-oleyl-1,3-diaminopropane. The molar ratio of phenol to formaldehyde to amine is preferably about 1:1:1.

When the aromatic Mannich is component (B)(II) the amine is a compound represented by the formula $$H_2NR^7OH$$

wherein $R^7$ is as defined above. In one embodiment this amine is monoethanolamine. The molar ratio of phenol to formaldehyde to amine is preferably about 2:2:1.

The preparation of the aromatic Manniehs (A), (B)(I) and (B)(II) can be carried out by a variety of methods known in the art. One method involves adding the phenol, the formaldehyde or precursor thereof, and the amine to a suitable vessel and heating to carry out the reaction. Reaction temperatures from about ambient up to about the decomposition temperature of any component or the aromatic Mannich product can be utilized. During reaction, water is drawn off as by sparging. Desirably, the reaction is carried out in solvent such as an aromatic type oil.

In another method of preparing the aromatic Mannichs, the phenol and the amine are added to a reaction vessel. The formaldehyde or precursor thereof is generally rapidly added and the exothermic reaction generated is supplemented by mild heat such that the reaction temperature is from about 60° C. to about 90° C. Desirably the addition temperature is less than the boiling point of water, otherwise, the water will bubble off and cause processing problems. After the reaction is essentially complete, the water by-product is removed in any conventional manner as by evaporation thereof which can be achieved by applying a vacuum, applying a sparge, heating or the like. A nitrogen sparge is often utilized at a temperature of from about 100° C. to about 130° C. Lower or higher temperatures can be utilized.

The copper reactant (C) can be a nitrate, nitrite, halide, carboxylate, phosphate, phosphite, sulfate, sulfite, carbonate, borate, hydroxide or oxide. These include Cu(I) and Cu(II) reagents. The copper compounds that are useful as the copper reactant (C) include cupric propionate, cupric acetate, cupric metaborate, cupric benzoate, cupric formate, cupric laurate, cupric nitrite, cupric oxychloride, cupric palmitate, cupric salicylate, copper carbonate and copper naphthenate. Copper carbonate is preferred.

The reaction by which the aromatic Mannich complexes of this invention are formed may be effected simply by mixing the aromatic Mannich reactant (A) or mixtures of aromatic Mannichs (B)(I) and (B)(II) with the copper reactant (C) at the desired temperature. The reaction can be carried out at a temperature of at least about 80° C. In some instances the reaction temperature may be as low as room temperature such as about 20° C. The upper limit for the reaction temperature is the decomposition point of the reaction mixture although a temperature higher than 250° C. is rarely necessary. In one embodiment the reaction temperature is no more than about 125° C., preferably no more than about 115° C., preferably no more than about 100° C., more preferably no more than about 90° C.

The reaction is preferably carried out in the presence of a diluent or solvent in which the reactants are soluble or the product is soluble. The solvent may be any fluid, inert solvent such as benzene, xylene, toluene, kerosene, mineral oil, chlorobenzene, dioxane or the like.

In one embodiment the reaction is carried out in the presence of an aromatic hydrocarbon solvent and then once the reaction is complete or substantially complete an effective amount of at least one alcohol is added to the product mixture to prevent the separation of viscous materials from the product mixture. Alcohols of 1 to about 18 carbon atoms can be used. In one embodiment the alcohol is isooctanol. The weight ratio of aromatic hydrocarbon solvent to alcohol can be from about 5:1 to about 0.5:1, preferably about 3:1 to about 1:1, more preferably about 2:1.

The relative amounts of the components (A), (B)(I), (B)(II) and (C) vary within wide ranges. The ratio of gram-moles of component (A) to gram-atoms of copper in component (C) is preferably from about 1.5:1 to about 3:1, more preferably about 2:1 to about 2.5:1, more preferably about 2.2:1. The molar ratio of (B)(I) to (B)(II) is preferably from about 2:1 to about 3:1, more preferably about 2.4:1 to about 2.5:1, more preferably about 2.50:1 to about 2.55:1. The ratio of gram-moles of the mixture of components (B)(I) and (B)(II) to gram-atoms of copper in component (C) is preferably from about 2:1 to about 3:1, more preferably about 2.2:1 to about 2.8:1, more preferably about 2.4:1 to about 2.6:1, more preferably about 2.50:1 to about 2.58:1.

The products obtained by the reaction of component (A) with component (C), or components (B)(I) and (B)(II) with component (C) are "organo-copper complexes". That is, it is believed to result from the combination of the functional groups in component (A) with the metal of component (C), or the functional groups in components (B)(I) and (B)(II) with the metal in component (C) by means of the secondary valence of the metal. The precise nature of the organocopper complex is not known. For purposes of this invention it is only necessary that such complexes be sufficiently stable in diesel fuel to permit use in a diesel engine equipped with an exhaust system particulate trap to lower the ignition temperature of exhaust particles collected in said trap.

The following examples illustrate the preparation of organocopper complexes that are used in accordance with the invention. Unless otherwise indicated, in the following examples as well as throughout the entire specification and in the appended claims, all parts and percentages are by weight, all pressures are atmospheric, and all temperatures are in degrees Centigrade.

EXAMPLE 1

Part A:

A mixture of 530 grams (2.0 moles) of p-propylenetetramerphenol, 700 grams (2.0 moles) of N-oleyl-1,3-diaminopropane, 66 grams (2.0 moles) of paraformaldehyde and 700 ml of toluene is heated under reflux conditions at 100°–120° C. for 3 hours in a reaction vessel equipped with a water trap. 45 ml of water are collected in the water trap. The mixture is stripped to a temperature of 120° C. at a pressure of 20 mm Hg absolute. The mixture is then filtered on a preformed 50 gram diatomaceous earth filter aid pad to provide 1220 grams of the desired product which is in the form of a light-brown oil.

Part B:

A mixture of 1590 grams (6.0 moles) of p-propylenetetramerphenol, 183 grams (3.0 moles) of monoethanolamine, 198 grams (6.0 moles) of paraformaldehyde and 800 ml of toluene is heated under reflux conditions at 100°–120° C. for 3 hours in a reaction vessel equipped with a water trap. 122 ml of water are collected in the water trap. The mixture is stripped to 120° C. at a pressure of 20 mm Hg absolute to provide the desired product which is in the form of a light yellow viscous oil.

Part C:

A mixture of 141 grams (0.227 mole) of the product from Part A, 55 grams (0.089 moles) of the product from Part B, and 100 ml of SC-100 Solvent (a product of Ohio Solvents identified as an aromatic hydrocarbon solvent) is heated to 40°–50° C. with stirring in a reaction vessel equipped with a water trap. 13.7 grams (0.124 mole) of $Cu_2CO_3(OH)_2$ are added to the mixture with stirring. The mixture is heated to 100° C. and maintained at that temperature for 1.5–2 hours until a clear green mixture forms. A small amount of water is collected in the water trap. The mixture is heated to 90°–100° C. at a pressure of 20–40 mm Hg absolute with stirring for one hour. 1.9 ml of water are collected in the water trap. 10 grams of diatomaceous filter aid are added to the mixture and the mixture is stirred for 0.5 hour. The temperature of the mixture is reduced to 60° C. The mixture is filtered over a preformed 20 gram diatomaeeous earth filter said pad to provide 190 grams of product which is in the form of a dark green oil. The product has a copper content of 3.0% by weight.

EXAMPLE 2

A mixture of 75.11 grams (0.5 mole) of p-t-butylphenol, 143.06 grams (0.51 mole) of oleylamine and 75 ml of toluene is heated in a reaction vessel to 70° C. 17.44 grams (0.535 mole) of paraformaldehyde are added to the mixture. The mixture is heated to 90° C. and maintained under reflux conditions for 1 hour. The reaction vessel is then equipped with a water trap. The mixture is maintained under reflux conditions for 1 hour. The mixture is blown with nitrogen at a rate of 0.25 scfh and maintained under reflux conditions for 2 hours. 10.92 grams of water are collected in the water trap. The mixture is cooled to 60° C. and the water trap is removed. 25.08 grams (0.227 mole) of $Cu_2CO_3(OH)_2$ are added to the mixture. 10.0 ml of ammonium hydroxide are added dropwise to the mixture over a period of 10 minutes. The mixture is heated to 90° C. and maintained under reflux conditions for 1 hour. The reaction vessel is teequipped with the water trap. The mixture is heated for 1 hour under reflux conditions and 12.8 grams of water are collected in the trap. The temperature of the mixture is increased to 145° C. and 50.8 grams of toluene are distilled out of the mixture. 111.94 grams of SC-100 Solvent are added to the mixture. The mixture is filtered through cloth to provide the desired product. The product has a copper content of 3.68% by weight.

EXAMPLE 3

A mixture of 75.11 grams (0.5 mole) of p-t-butylphenol, 143.06 grams (0.51 mole) of oleylamine and 134.6 grams of SC-100 Solvent is heated in a reaction vessel to 70° C. 17.44 grams (0.535 mole) of paraformaldehyde are added to the mixture. The mixture is heated to 80° C. and subjected to sufficient vacuum to permit the mixture to reflux at 80° C. The mixture is maintained under such reflux conditions for 1 hour. The reaction vessel is then equipped with a water trap. The mixture is maintained under the foregoing reflux conditions for an additional hour. The mixture is blown with nitrogen and maintained under the foregoing reflux conditions for 2 more hours. 8.5 grams of water are collected in the water trap. The mixture is cooled to 60° C. and the water trap is removed. 25.08 grams (0.227 mole) of $Cu_2CO_3(OH)_2$ are added to the mixture. 10.0 ml of ammonium hydroxide are added dropwise to the mixture over a period of 10 minutes. The mixture is subjected to a vacuum and maintained under reflux conditions at 80° C. for 1 hour. The reaction vessel was reequipped with the water trap. The mixture is heated for 3 hours under reflux conditions and 9 grams of water are collected in the trap. The temperature of the mixture is increased to 130° C. The mixture is cooled to room temperature and filtered through cloth to provide the desired product. The product has a copper content of 4.86% by weight.

EXAMPLE 4

A mixture of 75.11 grams (0.5 mole) of p-t-butylphenol, 143.06 grams (0.51 mole) of oleylamine and 80 grams of SC-100 Solvent is heated in a reaction vessel to 70° C. 17.44 grams (0.535 mole) of pareformaldehyde are added to the mixture. The mixture is heated to 80° C. The mixture is subjected to a sufficient vacuum to permit the mixture to reflux at 70° C. The mixture is maintained under such reflux conditions for 1 hour. The reaction vessel is then equipped with a water trap. The mixture is maintained under the above-identified reflux conditions for 2 hours. The mixture is blown with nitrogen at a ram of 0.25 scfh and maintained under the above-indicated reflux conditions for 1 hour. 7 grams of water are collected in the water trap. The mixture is cooled to 60° C. and the water trap is removed. 25.08 grams (0.227 mole) of $Cu_2CO_3(OH)_2$ are added to the mixture. 10.0 ml of ammonium hydroxide are added dropwise to the mixture over a period of 10 minutes. The mixture is subjected to sufficient vacuum to permit the mixture to reflux at 75° C. The mixture is maintained under such reflux conditions for 1 hour. The reaction vessel is reequipped with the water trap. The mixture is refluxed at 75° C. under vacuum for 2 hours. One gram of water is collected in the trap. The mixture is cooled to room temperature. 35.42 grams of SC-100 Solvent and 58.71 grams of isooctanol are added to the mixture. The mixture is filtered through cloth to provide 340.4 grams of the desired product. The product has a copper content of 3.89% by weight.

EXAMPLE 5

A mixture of 75.11 grams (0.5 mole) of p-t-butylphenol, 143.06 grams (0.51 mole) of oleylamine and 80 grams of SC-100 Solvent is heated in a reaction vessel to 70° C. 17.44 grams (0.535 mole) of paraformaldehyde are added to the mixture. The mixture is heated to 75° C. The mixture is subjected to a sufficient vacuum to permit the mixture to reflux at 80° C. The mixture is maintained under such reflux conditions for 1 hour. The reaction vessel is then equipped with a water trap. The mixture is maintained under the above-indicated reflux conditions for an additional 2 hours. The mixture is blown with nitrogen at a rate of 0.25 scfh and maintained under the above-indicated reflux conditions for 1 hour. One gram of water is collected in the water trap. The mixture is cooled to 60° C. and the water trap is removed. 25.08 grams (0.227 mole) of $Cu_2CO_3(OH)_2$ are added to the mixture. 10.0 ml of ammonium hydroxide are added dropwise to the mixture over a period of 10 minutes. The mixture is subjected to sufficient vacuum to permit the mixture to reflux at 80° C. The mixture is maintained under such reflux conditions for 1 hour. The reaction vessel is reequipped with the water trap. The mixture is heated to 115° C. for 2 hours and 5 grams of water are collected in the trap. After the first hour, the mixture is blown with nitrogen. The mixture is cooled to room temperature. 35.42 grams of SC-100 Solvent and 58.71 grams of isooctanol are added to the mixture. The mixture is filtered through cloth to provide 364.69 grams of the desired product. The product has a copper content of 3.63% by weight.

The diesel fuels that are useful with this invention can be any diesel fuel. In one embodiment the diesel fuel has a sulfur content of no more than about 0.1% by weight, preferably no more than about 0.05% by weight as determined by the test method specified in ASTM D 2622–87 entitled "Standard Test Method for Sulfur in Petroleum Products by X-Ray Spectrometry". Any fuel having a boiling range and viscosity suitable for use in a diesel-type engine can be used. These fuels typically have a 90% Point distillation temperature in the range of about 300° C. to about 390° C., preferably about 330° C. to about 350° C. The viscosity for these fuels typically ranges from about 1.3 to about 24 centistokes at 40° C. These diesel fuels can be classified as any of Grade Nos. 1-D, 2-D or 4-D as specified in ASTM D 975 entitled "Standard Specification for Diesel Fuel Oils". These diesel fuels can contain alcohols and esters.

The inventive diesel fuel compositions contain an effective amount of one or more of the inventive organo copper complexes described above to lower the ignition temperature of exhaust particulates formed on burning of the diesel fuel. The concentration of these organo copper complexes in the inventive diesel fuels is usually expressed in terms of the level of addition of the copper from such complexes. These diesel fuels preferably contain from 1 to about 5000 parts of copper per million parts of fuel, more preferably from about 1 to about 500 parts of copper per million parts of fuel, more preferably from 1 to about 100 parts of copper per million parts of fuel. In one embodiment the inventive diesel fuels contain from about 10 to about 50 parts of copper per million parts of fuel, preferably about 20 to about 40 parts of copper per million parts of fuel, more preferably about 30 parts of copper per million parts of fuel.

The inventive diesel fuel compositions can contain, in addition to the above-indicated organo copper complexes, other additives which are well known to those of skill in the art. These include antioxidants, dyes, octane improvers, rust inhibitors such as alkylated succinic acids and anhydrides, trialkylamines, bacteriostatic agents, gum inhibitors, metal deactivators, demulsifiers, upper cylinder lubricants and anti-icing agents.

These diesel fuel compositions can be combined with an ashless dispersant. Suitable ashless dispersants include esters of mono- or polyols and high molecular weight mono- or polycarboxylic acid acylating agents containing at least about 30 carbon atoms in the acyl moiety. Such esters are well known to those skilled in the art. See, for example, French Patent 1,396,645; British Patents 981,850; 1,055,337 and 1,306,529; and U.S. Pat. Nos. 3,255,108; 3,311,558; 3,331,776; 3,346,354; 3,522,179; 3,579,450; 3,542,680; 3,381,022; 3,639,242; 3,697,428; and 3,708,522. These patents are expressly incorporated herein by reference for their disclosure of suitable esters and methods for their preparation. When such dispersants are used, the weight ratio of the above-described organocopper complexes to the aforesaid ashless dispersant can be between about 0.1:1 and about 10:1, preferably between about 1:1 and about 10:1.

The organo copper complexes of this invention can be added directly to the fuel, or they can be diluted with a substantially inert, normally liquid organic diluent such as naphtha, benzene, toluene, xylene or a normally liquid fuel, to form an additive concentrate. These concentrates generally contain from about 1% to about 90% by weight of the organo copper complexes of this invention. In one embodiment the copper content of these concentrates is from about 0.5% to about 10% by weight, preferably about 1% to about 7% by weight, more preferably from about 2% to about 6% by weight, more preferably from about 3% to about 4% by weight. These concentrates may also contain one or more other conventional additives known in the art or described hereinabove.

In one embodiment of the invention the organo-copper complex is combined with the diesel fuel by direct addition, or as part of a concentrate as discussed above, and the diesel fuel is used to operate a diesel engine equipped with an exhaust system particulate trap. The diesel fuel containing the organo copper complex is contained in a fuel tank, transmitted to the diesel engine where it is burned, and the organo copper complex reduces the ignition temperature of exhaust particles collected in the exhaust system particulate trap.

In another embodiment, the foregoing operational procedure is used except that the organo-copper complex is maintained on board the apparatus being powered by the diesel engine (e.g., automobile, bus, truck, etc.) in a separate fuel additive dispenser apart from the diesel fuel. The organo copper complex is combined or blended with the diesel fuel during operation of the diesel engine. In this latter embodiment, the organo-copper complex that is maintained in the fuel additive dispenser can form a part of a fuel additive concentrate of the type discussed above, the concentrate being combined with the diesel fuel during operation of the diesel engine.

The following diesel fuel formulations are provided for purposes of exemplifying the invention. In the following diesel fuel formulations a Grade 2-D diesel fuel having a sulfur content of 0.05% by weight is used. The organocopper complexes from the indicated examples are used. The treatment level for the organocopper complex is expressed in parts per million (ppm) of copper that is added to the fuel. The remainder is the above-indicated low-sulfur diesel fuel which is expressed in terms of percent by weight.

| Fuel Formulation | Example | Copper (ppm) | Diesel Fuel (Wt %) |
| --- | --- | --- | --- |
| F-1 | 1 | 30 | 99.9000 |
| F-2 | 2 | 30 | 99.9223 |
| F-3 | 3 | 30 | 99.9383 |
| F-4 | 4 | 30 | 99.9229 |
| F-5 | 5 | 30 | 99.9174 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A method of operating a diesel engine equipped with an exhaust system particulate trap to reduce build-up of exhaust particles collected in said trap comprising operating said diesel engine with a diesel fuel containing an effective amount of at least one copper-containing complex to lower the ignition temperature of the exhaust particulates collected in said trap, said copper-containing complex being made by contacting either component (A) or component (B) with component (C); component (A) being at least one compound represented by the formula

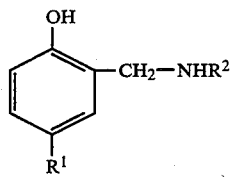

wherein $R^1$ is an alkyl group of 1 to about 6 carbon atoms, and $R^2$ is a saturated or unsaturated aliphatic hydrocarbyl group of about 16 to about 20 carbon atoms:
component (B) being a mixture of (B)(I) and (B)(II), component (B)(I) being at least one compound represented by the formula

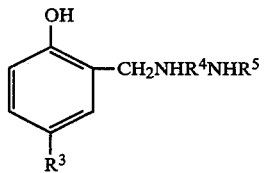

wherein $R^3$ is an alkyl group of about 9 to about 18 carbon atoms, $R^4$ is an alkylene group of 1 to about 4 carbon atoms, and $R^5$ is a saturated or unsaturated aliphatic hydrocarbyl group of about 16 to about 20 carbon atoms: and component (B)(II) is at least one compound represented by the formula

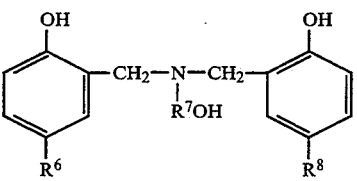

wherein $R^6$ and $R^8$ are independently alkyl groups of about 9 to about 18 carbon atoms, and $R^7$ is an alkylene group of 1 to about 4 carbon atoms; and
component (C) is at least one copper reactant.

2. The method of claim 1 wherein $R^1$ is t-butyl and $R^2$ is oleyl.

3. The method of claim 1 wherein $R^3$ has about 12 carbon atoms, $R^4$ is propylene and $R^5$ is oleyl.

4. The method of claim 1 wherein each of $R^6$ and $R^8$ have about 12 carbon atoms and $R^7$ has about 2 or about 3 carbon atoms.

5. The method of claim 1 wherein component (C) is copper carbonate.

6. The method of claim 1 wherein the ratio of gram-moles of (A) to gram-atoms of copper in (C) is from about 1.5:1 to about 3:1.

7. The method of claim 1 wherein the molar ratio of (B)(I) to (B)(II) is from about 2:1 to about 3:1.

8. The method of claim 1 wherein the ratio of the total gram-moles of the mixture of (B)(I) and (B)(II) to gram-atoms of copper in (C) is from about 2:1 to about 3:1.

9. A method of operating a diesel engine equipped with an exhaust system particulate trap to reduce build-up of exhaust particles collected in said trap comprising operating said diesel engine with a diesel fuel containing an effective amount of at least one copper-containing complex to lower the ignition temperature of the exhaust particulates collected in said trap, said cooper-containing complex being made by contacting
(A) a compound represented by the formula

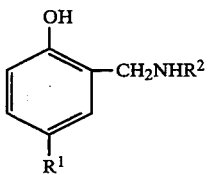

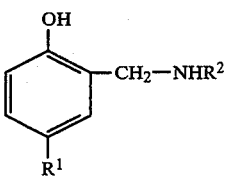

wherein $R^1$ is t-butyl and $R^2$ is oleyl; and
(C) copper carbonate;
the ratio of gram-moles of (A) to gram-atoms of copper in (C) being about 1.5:1 to about 3:1.

10. A method of operating a diesel engine equipped with an exhaust system particulate trap to reduce build-up of exhaust particles collected in said trap comprising operating said diesel engine with a diesel fuel containing an effective amount of at least one copper-containing complex to lower to lower the ignition temperature of the exhaust particulates collected in said trap, said copper-containing complex being made by contacting (B)(I) at least one compound represented by the formula

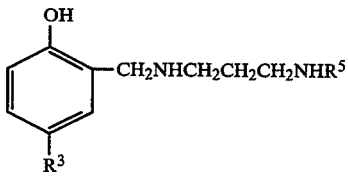

wherein $R^3$ is an alkyl group of about 12 carbon atoms and $R^5$ is oleyl;

(B)(II) at least One compound represented by the formula

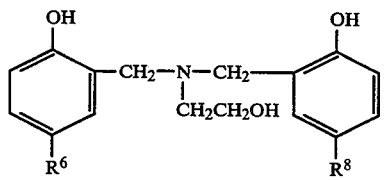

wherein $R^6$ and $R^8$ are each alkyl groups of about 12 carbon atoms; and (C) copper carbonate;

the molar ratio of (B)(I) to (B)(II) being from about 2:1 to about 3:1; and the ratio of total gram-moles of (B)(I) and (B)(II) to gram-atoms of copper in (C) being from about 2:1 to about 3:1.

11. A method of operating an apparatus powered by a diesel engine and equipped with a fuel additive dispenser and an exhaust system particulate trap comprising:

operating said engine using a diesel fuel;

maintaining a fuel additive comprising at least one copper-containing complex in said fuel additive dispenser;

blending an effective amount of said fuel additive with said diesel fuel to reduce the ignition temperature of exhaust particulates collected in said trap;

said copper-containing complex being made by contacting either component (A) or component (B) with component (C);

component (A) being at least one compound represented by the formula

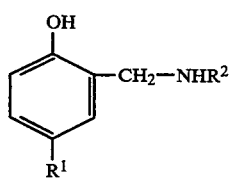

wherein $R^1$ is an alkyl group of 1 to about 6 carbon atoms, and $R^2$ is a saturated or unsaturated aliphatic hydrocarbyl group of about 16 to about 20 carbon atoms;

component (B) being a mixture of (B)(I) and (B)(II), component (B)(I) being at least one compound represented by the formula

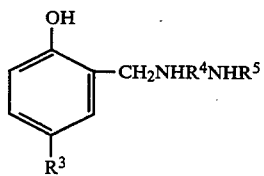

wherein $R^3$ is an alkyl group of about 9 to about 18 carbon atoms, $R^4$ is an alkylene group of 1 to about 4 carbon atoms, and $R^4$ is a saturated or unsaturated hydrocarbyl group of about 16 to about 20 carbon atoms; and component (B)(II) is at least one compound represented by the formula

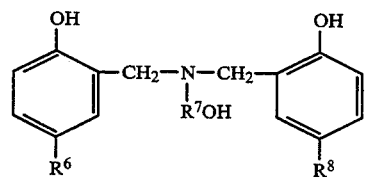

wherein $R^6$ and $R^8$ are independently alkyl groups of about 9 to about 18 carbon atoms, and $R^7$ is an alkylene group of 1 to about 4 carbon atoms; and component (C) is at least one copper reactant.

12. A method of operating an apparatus powered by a diesel engine and equipped with a fuel additive dispenser and an exhaust system particulate trap comprising:

operating said engine using a diesel fuel;

maintaining a fuel additive comprising at least one copper-containing complex in said fuel additive dispenser;

blending an effective amount of said fuel additive with said diesel fuel to reduce the ignition temperature of exhaust particulates collected in said trap;

said copper-containing complex being made by contacting (A) a compound represented by the formula

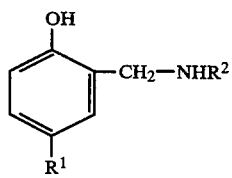

wherein $R^1$ is t-butyl and $R^2$ is oleyl; and (C) copper carbonate;

the ratio of gram-moles Of (A) to gram-atoms of copper in (C) being about 1:5:1 to about 3:1.

13. A method of operating an apparatus powered by a diesel engine and equipped with a fuel additive dispenser and an exhaust system particulate trap comprising:

operating said engine using a diesel fuel;

maintaining a fuel additive comprising at least one copper-containing complex in said fuel additive dispenser;

blending an effective amount of said fuel additive with said diesel fuel to reduce the ignition temperature of exhaust particulates collected in said trap;

said copper-containing complex being made by contacting (B)(I) at least one compound represented by the formula

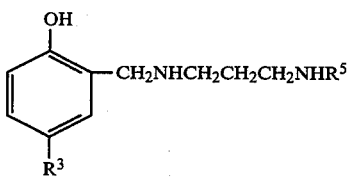

wherein $R^3$ is an alkyl group of about 12 carbon atoms and $R^5$ is oleyl;

(B)(II) at least one compound represented by the formula

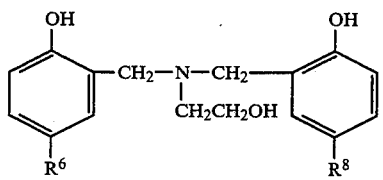

wherein $R^6$ and $R^8$ are each alkyl groups of about 12 carbon atoms; and (C) copper carbonate;

the molar ratio of (B)(I) to (B)(II) being from about 2:1 to about 3:1; and the ratio of total gram-moles of (B)(I) and (B)(II) to gram-atoms of copper in (C) D being from about 2:1 to about 3:1.

* * * * *